US006344330B1

(12) United States Patent
Ellman et al.

(10) Patent No.: US 6,344,330 B1
(45) **Date of Patent: *Feb. 5, 2002**

(54) PHARMACOPHORE RECOMBINATION FOR THE IDENTIFICATION OF SMALL MOLECULE DRUG LEAD COMPOUNDS

(75) Inventors: Jonathan A. Ellman, Oakland; Ingrid Choong, Berkeley, both of CA (US)

(73) Assignee: The Regents of the University of California, Oakland, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/049,754

(22) Filed: Mar. 27, 1998

(51) Int. Cl.[7] .................... A61K 31/335; C07D 311/02; G01N 33/53; G01N 33/566; C12G 1/68

(52) U.S. Cl. ........................ 435/7.1; 549/283; 549/284; 549/285; 549/286; 549/287; 549/288; 549/289; 549/290; 435/6; 435/7.2; 436/501; 436/518; 424/1.11; 424/9.1; 424/178.1; 424/19.1; 530/345; 530/389.1; 530/402; 530/807; 514/449; 514/450; 514/451; 514/452; 514/453; 514/454; 514/455; 514/456; 514/457; 514/458

(58) Field of Search ............................. 435/7.1, 7.2, 6; 436/501, 518; 424/1.11, 9.1, 178.1, 193.1; 530/345, 389.1, 402, 807; 514/449–458; 549/283–290

(56) References Cited

U.S. PATENT DOCUMENTS

| | | | | |
|---|---|---|---|---|
| 4,727,022 | A | 2/1988 | Skold et al. | 435/7 |
| 5,362,859 | A | 11/1994 | Zale | 530/413 |
| 5,422,281 | A | 6/1995 | Harris et al. | 436/501 |
| 5,512,435 | A | 4/1996 | Renschler et al. | 435/6 |
| 5,543,507 | A | 8/1996 | Cook et al. | 536/23.1 |
| 5,658,727 | A | 8/1997 | Barbas et al. | 435/6 |
| 5,683,867 | A | 11/1997 | Biesecker et al. | 435/6 |
| 5,698,401 | A | 12/1997 | Fesik et al. | |

FOREIGN PATENT DOCUMENTS

| | | |
|---|---|---|
| WO | WO 98/11436 | 3/1998 |

OTHER PUBLICATIONS

Sigal et al. Polyacrylamides Bearing Pendant a–Sialoside Groups Strongly Inhibit Agglutination of Erythrocyes by Influenza Virus . . . J. Am. Chem. Soc. vol. 118, No. 16, pp. 3789–3400, Apr. 1996.*

Boger et al. Solution–Phase Combinatorial Synthesis via the Olefin Metathesis Reaction. Bioorg. Med. Chem. Lett., vol. 7, No. 4, pp. 463–468, Feb. 1997.*

Gordon et al. Applications of Combinatorial Techniques to Drug Discovery. 2. Combinatorial Organic Synthesis, Library Screening Strategies and Future Directions. J. Med. Chem., vol. 37, No. 10, pp. 1385–1401, May 1994.*

Keyes et al. Correlation of Anti–HIV Potency with Lipophilicity in a Series of Cosalane Analogs . . . J. Med. Chem., vol. 39, No. 2, pp. 508–514, Jan. 1996.*

Hajduk et al. J. Med. Chem. vol. 40, No. 20, pp. 3144–3150, Sep. 1997.*

Shuker et al., *Science* 274:1531–1534 (1996).

Singh et al., *J. Am. Chem. Soc.* 118:1669–1676 (1996).

Weber et al., *Angew. Chem. Int. Ed. Engl.* 34:2280–2282 (1995).

Huc et al., *Proc. Natl. Acad. Sci. USA* 94:2106–2110 (1997).

Holland, *Scientific American* Jul. 1992, pp. 66–72 (1992).

Rowan et al., *Angew. Chem. Int. Ed. Engl.* 35:2143–2145 (1996).

Rowan et al., *J. Am. Chem. Soc.* 119:2578–2579 (1997).

Baldwin, et al., *J. Am. Chem. Soc.*, 117:5588–5589 (1995).

Gilbertson et al., *Tetrahedron Letters* 37:6475–6478 (1996).

Pfistermueller, et al., *FEBS Letters* 39:14–20 (1996).

Godfrey, et al., *J. Exp. Med.* 80:757–762 (1994).

Rose, *J. Amer. Chem. Soc.* 116:30–33 (1994).

Shao et al., *Amer. Chem. Soc.* 117:3893–3899 (1995).

Tuchscherer, *Eng.*, 34:8419–8422 (1993).

Jencks, *Proc. Natl. Acad. Sci*, 78:4046–4050 (1981).

Olejniczak et al., *J. of Am. Chem. Soc*, 119:5828–5832 (1997).

(List continued on next page.)

*Primary Examiner*—Jyothsna Venkat
*Assistant Examiner*—Maurie E. Garcia
(74) *Attorney, Agent, or Firm*—Foley & Lardner

(57) ABSTRACT

The present invention is directed to novel methods for identifying small molecule ligands that are capable of binding with high affinity to a biological target molecule of interest. High affinity binding ligands identified by the described methods find use, for example, as small molecule lead compounds that may they themselves be, or may give rise to, novel therapeutic drugs. More specifically, the subject invention is directed to methods for identifying a ligand that binds to a target biological molecule of interest, wherein a population of small organic compounds are selected and then "pre-screened" to identify those that are capable of binding to the molecular target. The small organic compounds that are identified during the pre-screening as being capable of binding to the target (or structurally related analogs thereof) are then coupled in various combinations with a linker element to provide a library of potential ligands for binding to the target molecule that is then screened to identify ligands having very high binding affinities for the molecular target. Ligands obtained by this method and methods for using those ligands for inhibiting the interaction between two biological molecules are also provided.

23 Claims, 8 Drawing Sheets

OTHER PUBLICATIONS

Nakamura et al., *Biochemistry* 24:1364–1376 (1985).

Nazarpack–Kandlousy et al., *J. Combinatorial Chem.* (1998).

Hajduk, et al., *J. Am. Chem. Soc.* 119:5818–5827 (1997).

Dolle et al., *J. of Combinatorial Chem.* 1:229–382 (1999).

Puius et al. *Proc. Natl. Acad. Sci.* 94:13420–13425 (1997).

Eliseev *Drug Discovery and Development* 1:106–115 (1998).

Jindal, et al., *Spectrum Drug Discovery and Design*, 20:1–15 (1998).

Hajduk, et al., 1997, *Science* 278:497–499.

* cited by examiner

Chromones

Phenols

Furans

Phenoxides

Diverse

1

2 (n = 2 - 5)

PHARMACOPHORE RECOMBINATION FOR THE IDENTIFICATION OF SMALL MOLECULE DRUG LEAD COMPOUNDS

This invention was made with Government support under Contract No. R01 GM50353 awarded by the National Institutes of Health. The Government has certain rights to this invention.

FIELD OF THE INVENTION

The present invention is directed to novel methods for identifying small molecule drug lead compounds.

BACKGROUND OF THE INVENTION

In response to the ever increasing demand for novel compounds useful in the effective treatment of various maladies, the medical research community has developed a number of different strategies for discovering and optimizing new therapeutic drugs. For the most part, these strategies are dependent upon molecular techniques that allow the identification of tightly binding ligands for a given biological target molecule. Once identified, these ligands may then carry out their therapeutic functions by activating, inhibiting or otherwise altering the activity of the molecular target to which they bind.

In one such strategy, new therapeutic drugs are identified by screening combinatorial libraries of synthetic small molecule compounds, determining which compound(s) have the highest probability of providing an effective therapeutic and then optimizing the therapeutic properties of the identified small molecule compound(s) by synthesizing structurally related analogs and analyzing them for binding to the target molecule (Gallop et al., *J. Med. Chem.* 37:1233–1251 (1994), Gordon et al., *J. Med. Chem.* 37:1385–1401 (1994), Czarnik and Ellman, *Acc. Chem. Res.* 29:112–170 (1996), Thompson and Ellman, *Chem. Rev.* 96:555–600 (1996) and Balkenhohl et al., *Angew. Chem. Int. Ed.* 35:2288–2337 (1996)). However, this process is not only time consuming and costly, it often does not provide for the successful identification of a small molecule compound having sufficient therapeutic potency for the desired application. For example, while the preparation and evaluation of combinatorial libraries of small molecules has proven somewhat useful for new drug discovery, the identification of small molecules for difficult molecular targets (e.g., such as those useful for blocking or otherwise taking part in protein-protein interactions) has not been particularly effective (Brown, *Molecular Diversity* 2:217–222 (1996)).

One issue that limits the success of combinatorial library approaches is that it is possible to synthesize only a very small fraction of the possible number of small molecules. For example, greater than $10^{60}$ different small molecules having valid chemical structures and molecular weights under 600 daltons can be envisioned. However, even the most ambitious of small molecule combinatorial library efforts have been able to generate libraries of only tens to hundreds of millions of different compounds for testing. Therefore, combinatorial technology allows one to test only a very small subset of the possible small molecules, thereby resulting in a high probability that the most potent small molecule compounds will be missed. Thus, suitable small molecule compounds having the required availability, activity or chemical and/or structural properties often cannot be found. Moreover, even when such small molecule compounds are available, optimization of those compounds to identify an effective therapeutic often requires the synthesis of an extremely large number of structural analogs and/or prior knowledge of the structure of the molecular target for that compound. Furthermore, screening large combinatorial libraries of potential binding compounds to identify a lead compound for optimization can be difficult and time-consuming because each and every member of the library must be tested. It is evident, therefore, that novel methods for rapidly and efficiently identifying new small molecule drug leads are needed.

Living organisms evolve through a process that includes both (1) genetic recombination, where sexual reproduction acts to mix and recombine the attributes of the parent organisms to provide progeny having attributes of both parents, and (2) natural selection, where only those progeny that are sufficiently "fit" are capable of passing their attributes on to the next generation. Approaches that closely model the process by which organism evolve have previously been reported for identifying small molecules that bind to receptors and enzymes (Weber et al., *Angew. Chem. Int. Ed. Engl.* 34:2280–2282 (1995) and Singh et al., *J. Am. Chem Soc.* 118:1669–1676 (1996)). These approaches are based upon the mathematical method termed "genetic algorithms" (Holland, *Sci. Am.* 66–72 (1992)). Using genetic algorithms, a population of different compounds is screened to identify the compounds that bind to the receptor or enzyme (i.e., the "fittest" compounds). A population of progeny compounds is then prepared by recombining the building blocks that were used to prepare the "fittest" compounds. A screen is then performed to identify the compounds that bind to the target with the highest affinity, which are made up of the optimal building block combinations.

However, because the building blocks employed in the genetic algorithm approach are not preselected, one of two techniques are used to identify tight binding ligands: (1) extremely large populations of compounds must be screened and recombined, or (2) multiple rounds of screening and recombination are performed on relatively small populations where additional building blocks are gradually introduced through a process that is analogous to genetic mutation. In this second approach, many rounds of selection, recombination and building block introduction are required to identify the optimal building block combinations in analogy to the many rounds of selection, reproduction and mutation that are required in the evolution of living organisms. Thus, the use of genetic algorithms is currently limited because of the large amount of time required for compound preparation and screening, wherein the goal of new drug discovery is to identify a potent compound as quickly as possible.

Another recently reported approach for identifying high affinity ligands for molecular targets of interest is by determining structure-activity relationships from nuclear magnetic resonance analysis, i.e., "SAR by NMR" (Shuker et al., *Science* 274:1531–1534 (1996) and U.S. Pat. No. 5,698,401 by Fesik et al.). In this approach, the physical structure of a target protein is determined by NMR and then small molecule building blocks are identified that bind to the protein at nearby points on the protein surface. Adjacently binding small molecules are then coupled together with a linker in order to obtain compounds that bind to the target protein with higher affinity than the unlinked compounds alone. Thus, by having available the NMR structure of the target protein, the lengths of linkers for coupling two adjacently binding small molecules can be determined and small molecule ligands can be rationally designed. This approach has been useful for identifying compounds that bind to FK506 binding protein with a $K_d$=20 nM (Shuker et al., supra) and to stromelysin with a $K_d$=15 nM (Hajduk et al., *J. Am. Chem. Soc.* 119:5818–5827 (1997) and Hajduk et al., *J. Am. Chem. Soc.* 119:5828–5832 (1997)).

However, while the SAR by NMR method is powerful, it also has serious limitations. For example, the approach requires huge amounts of target protein (>200 mg) and this protein typically must be $^{15}$N-labeled so that it is useful for NMR studies. Moreover, the SAR by NMR approach usually requires that the target protein be soluble to >0.3 mM and have a molecular weight less than about 25–30 kDa. Additionally, the structure of the target protein is first resolved by NMR, a process which often can require a 6 to 12 month time commitment.

From the above, it is evident that there is a need for novel techniques useful for rapidly and efficiently identifying small molecule drug lead compounds that are capable of binding with high affinity to a molecular target of interest. We herein describe for the first time a method which is based upon pharmacophore recombination, wherein a population of small molecule pharmacophores are "pre-selected" for the ability to bind to a molecular target and wherein the small molecule pharmacophores that bind with the highest affinity are then chemically linked in various combinations to provide a library of potential high affinity a binding ligands. The library of potential binding ligands is then screened using a simple functional assay for the presence of one or more compounds that bind to the target molecule with very high affinity.

SUMMARY OF THE INVENTION

Applicants herein describe a molecular approach for rapidly and efficiently identifying small molecule ligands that are capable of binding to a biomolecular target with high affinity, wherein ligand compounds identified by the subject method may find use, for example, as new small molecule drug leads. The herein described methods allow a population of only the most favorable compounds to be assayed for binding to a target biomolecule without the need for screening all possible small molecule compounds and combinations thereof for binding to the target as is required in standard combinatorial library approaches. More specifically, a population of small organic molecules is initially selected and then "pre-screened" to identify a subset of that population that bind to a molecular target with or below a certain dissociation constant. Those organic molecules identified during this "pre-screening" step as being capable of binding to the biological target are then coupled in a variety of combinations using one or more linker elements to provide a library of potential high affinity binding ligands, whose building blocks represent the small organic molecules having the highest affinity for the biological target as identified in the "pre-screening" step. The library of potential ligands for binding to the target molecule is then screened to identify those members that exhibit the lowest dissociation constant for binding to the molecular target. Because the library of small organic molecule building blocks is initially "pre-screened" to select for a much smaller set of the most favorable building blocks, the most productive building block and linker combinations can be identified without the laborious task of screening all possible combinations of all organic molecule building blocks coupled together by a set of linkers. The process of identifying high affinity binding ligands is therefore, greatly expedited.

With regard to the above, one embodiment of the present invention is directed to a method for identifying a ligand that binds to a biological target molecule of interest, wherein the method comprises the steps of:

(a) selecting a population of organic compounds that are capable of being chemically coupled by a linker element to provide potential ligands for binding to the target molecule;

(b) screening the population of organic compounds to identify at least first and second organic compounds which bind to the target molecule;

(c) chemically coupling the at least first and second organic compounds or structurally related analogs thereof with a linker element to provide a library of potential ligands for binding to the target molecule; and (d) screening the library obtained in step (c) to identify a ligand that binds to the biological target molecule.

In various preferred embodiments, the population of organic compounds may comprise compounds of less than 500 daltons, may comprise simple aldehydes, amines, alcohols, carboxylic acids, thiols, aryl halides, alkenes, alkynes, ketones, ethers and/or oximes and/or may bind to the target biomolecule with a $K_d$ of 10 mM or lower. In a particularly preferred embodiment, the population of organic compounds may comprise oxime compounds, wherein the structurally related aldehyde analogs of those oxime compounds are capable of being chemically coupled via a bis-hydroxylamine linker element. Biological target molecules that find use in the described methods include, for example, proteins, nucleic acids and saccharides, preferably proteins.

In other preferred embodiments, the potential high affinity ligand molecules prepared by chemically coupling the organic compounds identified as being capable of binding to the target biomolecule are preferably dimeric molecules of less than about 1000 daltons in size and/or comprise compounds that bind to the molecular target with a $K_d$ of about 500 $\mu$M or lower.

Another embodiment of the present invention is directed to a method for inhibiting the interaction between first and second biological molecules, wherein the method comprises the step of contacting a system comprising both the first and second biological molecules with a binding inhibitory amount of a ligand identified by the above described method, wherein the ligand binds to one of the first or second biological molecules and inhibits their ability to interact.

A further embodiment of the present invention is directed to a pharmacophore molecule that binds to a biological target molecule of interest which is obtained by a process comprising reactively coupling two or more aldehydes with a bis-hydroxylamine linker element.

Additional embodiments of the present invention will become evident to the ordinarily skilled artisan upon a review of the present specification.

DETAILED DESCRIPTION OF THE INVENTION

Figure 1:
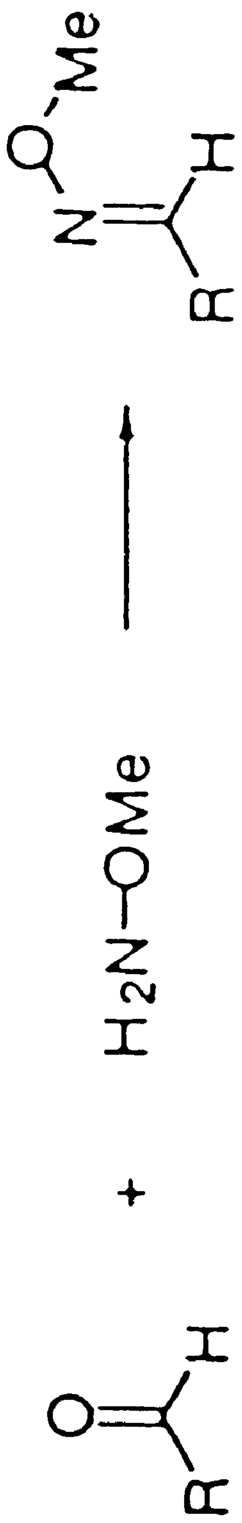
FIG. 1 shows a synthetic reaction wherein an aldehyde is reacted with O-methyl hydroxylamine to produce an O-methyl oxime compound.

The present invention provides a rapid and efficient method for identifying small molecule ligands that are capable of binding with high affinity to biological target molecules of interest. The compounds identified by the subject method find use, for example, as lead compounds for the development of novel therapeutic drugs The subject methods involve the selection of a population of small organic molecules which are capable of being chemically coupled via a linker element and wherein the population of organic molecules may be "pre-screened" in order to identify members of the population that are capable of binding to a molecular target. At least a portion of the small organic molecules identified during the "pre-screen" as being capable of binding to the target are then chemically linked to one another in various combinations to provide a library of potential ligands for binding to the target biomolecule. The library of potential high affinity ligands is then screened to identify ligands that bind to the molecular target with high affinity. The step of "pre-screening" the library of small organic molecules to identify those that are capable of binding to the target allows one to limit the library of potential binding ligands to only those that are comprised of the most favorable organic building blocks, thereby decreasing the required complexity of the library of potential ligands while increasing the probability of identifying a ligand exhibiting high binding affinity for the biological target molecule.

One embodiment of the present invention is directed to a method for identifying a ligand that binds to a biological target molecule of interest. The subject method involves selecting a population of organic compounds that are capable of being chemically coupled via a linker element to provide potential ligands for binding to the target biomolecule. In this regard, the phrase "selecting a population of organic compounds" is to be construed broadly and is intended to encompass all means by which one may obtain a population comprising two or more organic compounds which include, for example, obtaining such compounds from a commercial or non-commercial source, synthesizing such compounds using standard chemical synthesis technology or combinatorial synthesis technology (see Gallop et al. (1994), supra, Gordon et al. (1994), supra, Czarnik and Ellman (1996), supra, Thompson and Ellman (1996), supra and Balkenhohl et al. (1996) supra) and obtaining such compounds as degradation products from larger precursor compounds, e.g. known therapeutic drugs, large chemical molecules, and the like.

The "organic compounds" of the present invention are, for the most part, small chemical molecules that have one or more chemically reactive functionalities (or sites that may be readily converted to a chemically reactive functionality using standard technology) that provide a site for coupling to another organic compound via a chemically reactive linker element. Thus, the organic compounds of the present invention are capable of being chemically coupled to one another via a linker element to provide potential ligands for binding to the target molecule, meaning that the organic compounds have a reactive functionality, or a site that can be readily chemically converted to a reactive functionality, where a linker element may covalently attach thereto, thereby allowing multimerization of the organic compounds through linkage to the linker. "Ligands" or "potential ligands for binding to a target molecule" for purposes herein are compounds that are obtained from reacting two or more organic compounds, which may be the same or different, preferably different, with one or more linker element(s) so as to produce a molecule comprising the two or more organic compounds and the one or more linker element.

Monomeric compounds that find use in the present invention include, for example, aldehydes, ketones, oximes, such as O-alkyl oxioms, preferably O-methyl oximes, hydrazones, semicarbazones, carbazides, primary amines, secondary amines, such as N-methylamines, tertiary amines, such as N,N-dimethylamines, N-substituted hydrazines, hydrazides, alcohols, ethers, thiols, thioethers, thioesters, disulfides, carboxylic acids, esters, amides, ureas, carbamates, carbonates, ketals, thioketals, acetals, thioacetals, aryl halides, aryl sulfonates, alkyl halides, alkyl sulfonates, aromatic compounds, heterocyclic compounds, anilines, alkenes, alkynes, diols, amino alcohols, oxazolidines, oxazolines, thiazolidines, thiazolines, enamines, sulfonamides, epoxides, and aziridines, and the like, all of which have chemically reactive functionalities (or are directly prepared from precursor compounds that have chemically reactive functionalities) capable of linking, either directly or indirectly, to a linker element. In fact, virtually any small organic molecule that is capable of being chemically coupled to another small organic molecule may find use in the present invention with the proviso that it is sufficiently soluble in aqueous solutions to be tested for its ability to bind to a biomolecular target.

The above described organic compounds will serve as the individual building blocks for ligand molecules prepared therefrom. Organic compounds that find use herein will generally be less than about 2000 daltons in size, usually less than about 1500 daltons in size, more usually less than about 750 daltons in size, preferably less than about 500 daltons in size, often less than about 250 daltons in size and more often less than about 200 daltons in size, although organic molecules larger than 2000 daltons in size will also find use herein. Organic molecules that find use may be employed in the herein described method as originally obtained from a commercial or non-commercial source (for example, a large number of small organic chemical compounds are readily obtainable from commercial suppliers such as Aldrich Chemical Co., Milwaukee, Wis. and Sigma Chemical Co., St. Louis, Mo.) or may be obtained by chemical synthesis. Examples of the latter include the preparation of a population of organic oxime compounds from a single step condensation of commercially available aldehydes with O-alkyl hydroxylamine as described in Example I below and the preparation of a library of N,N-dimethylamine monomer compounds from the reductive amination of commercially available aldehydes and dimethylamine using support-bound triacetoxyborohydride as described in Example II below and by Kaldor et al., *Tetrahedron Lett.* 37:7193–7196 (1996).

Populations of organic compounds which find use herein will generally comprise at least 2 organic compounds, often at least about 25 different organic compounds, more often at least about 100 different organic compounds, usually at least about 500 different organic compounds, more usually at least about 1000 different organic compounds, preferably at least about 2500 different organic compounds, more preferably at least about 5000 different organic compounds and most preferably at least about 10,000 or more different organic compounds. Populations may be selected or constructed such that each individual molecule of the population may be spatially separated from the other molecules of the population (e.g., each member of the library is a separate microtiter well) or two or more members of the population may be combined if methods for deconvolution are readily available. The methods by which the populations of organic compounds are prepared will not be critical to the invention.

Once selected, a population of organic compounds will be screened using one of any number of different known assays for the purpose of identifying organic molecules that are capable of binding to a biological target molecule of interest. "Biological target molecules", "target biological molecules", "target biomolecules", "molecular targets", "biological targets", and other grammatical equivalents refer to biological molecules that are available (either commercially, recombinantly, synthetically or otherwise) in sufficient quantities for use in in vitro binding assays and for which there is some interest for identifying a high affinity binding partner. For the most part, target biomolecules are proteins, including proteins that may be associated with a human disease condition, such as cell surface and soluble receptor proteins, such as lymphocyte cell surface receptors, enzymes, such as proteases, clotting factors, serine/threonine kinases and dephosphorylases, threonine kinases and dephosphorylases, bacterial enzymes, fungal enzymes and viral enzymes, signal transduction molecules, transcription factors, proteins associated with DNA and/or RNA synthesis or degradation, immunoglobulins, hormones, receptors for various cytokines including, for example, erythropoietin/EPO, granulocyte colony stimulating receptor, granulocyte macrophage colony stimulating receptor, thrombopoietin (TPO), IL-2, IL-3, IL-4, IL-5, IL-6, IL-10, IL-11, IL-12, growth hormone, prolactin, human placental lactogen (LPL), CNTF, octostatin, various chemokines and their receptors such as RANTES, MIP1-α, IL-8, various ligands and receptors for tyrosine kinase such as insulin, insulin-like growth factor 1 (IGF-1), epidermal growth factor (EGF), heregulin-α and heregulin-β, vascular endothelial growth factor (VEGF), placental growth factor (PLGF), tissue growth factors (TGF-α and TGF-β), other hormones and receptors such as bone morphogenic factors, folical stimulating hormone (FSH), and leutinizing hormone (LH), tissue necrosis factor (TNF), apoptosis factor-1 and -2 (AP-1 and AP-2), and proteins and receptors that share 20% or more sequence identity to these, and the like, nucleic acids, including both DNA and RNA, saccharide complexes, and the like.

For the step of screening populations of organic compounds for members having the ability to bind to a target biomolecule of interest, a simple ELISA assay may be used to (a) identify member(s) of the population that are capable of binding to the target, and (b) determine the approximate $K_d$ with which the library member(s) bind to the molecular target. While ELISA assays are preferred for screening libraries of organic compounds, virtually any in vitro assay that allows one to detect binding of the target biomolecule by an organic compound may be employed for screening the library, wherein such assays include ELISA, other sandwich-type binding assays, binding assays which employ labeled molecules such as radioactively or fluorescently labeled molecules, fluorescence depolarization, calorimetry, protein denaturation, resistance to proteolysis, gel filtration, equilibrium dialysis, surface plasmin resonance, X-ray crystallography, and the like. Such assays either measure the ability of organic compound library members to bind directly to the molecular target or are competition binding assays designed to measure the ability of organic compounds to inhibit the interaction between the molecular target and another molecule that binds to the molecular target. Any of the above assays may be employed to screen libraries of organic compounds to identify those that bind to a molecular target.

For the step of screening a population of organic compounds to identify those that bind to a target biomolecule, it will be well within the skill level in the art to determine the concentration of the organic compounds to be employed in the binding assay. For the most part, the screening assays will employ concentrations of organic compounds ranging from about 0.01 to 50 mM, preferably from about 0.01 to 10 mM.

The step of screening a library of organic compounds to identify those that bind to a target biomolecule allows one to identify and isolate only those members of the library that have some binding affinity for the target. As such, in contrast to standard combinatorial library approaches, because the small organic building blocks are "pre-screened" to select a much smaller set of organic compounds that have some binding affinity for the target, the most productive organic compound building blocks can be identified for incorporation into the potential high affinity binding ligands that are prepared therefrom, without having to screen all possible combinations of all of the initial organic compound building blocks. Generally, the organic compound library members selected as building blocks for subsequently prepared ligand compounds are those that have the highest affinity for binding to the target biomolecule. For the most part, organic compounds chosen as building blocks for incorporation into the subsequently prepared ligand compounds are those that bind to the target biomolecule with a $K_d$ of about 10 mM or less, usually about 5 mM or less, more usually about 1 mM or less, preferably about 500 μM or less, more preferably about 100 μM or less and most preferably about 50 μM or less. However, for some applications, one or more of the organic compounds chosen for incorporation into the subsequently prepared potential ligand compounds may have an individual $K_d$ for the target biomolecule of greater than 10 mM.

Once organic compounds that bind to a target biomolecule with some desired degree of affinity are identified, at least a portion of those organic compounds (or structurally related analogs thereof) are chemically coupled via a linker element to provide a library of potential ligands for binding to the target molecule, wherein those potential ligands comprise at least two organic compounds (or structurally related analogs thereof) linked by a linker element. The organic compounds or analogs thereof incorporated into a potential ligand compound may be the same (i.e., to provide a homomultimer) or different (i.e., to provide a heteromultimer), usually different. By "structurally related analog", "analog", and the like, is meant an organic compound that has the same chemical structure as an organic compound identified as being capable of binding to the target molecule except that the analog has a different chemically reactive functionality for binding to the linker than does the organic compound that was identified as being capable of binding to the target. The analog may also optionally possess or lack one or more substituents that are either lacking or present, respectively, on the organic compounds identified in the pre-screening provided that the presence or absence of those substituents does not substantially alter the compounds ability to bind to the target. As such, while one may pre-screen a population of, for example, organic oxime compounds to identify oxime compounds that bind to the target biomolecule, one can chemically couple not the actual oxime compounds identified in the "pre-screening" but rather aldehydes having that same chemical structures as the oximes identified in the a screen (but which have an aldehyde reactive functionality rather than an oxime reactive functionality). The present invention, therefore, encompasses not only chemical coupling of the actual organic compounds identified in the initial "pre-screening step" (e.g., aldehydes are pre-screened and also subsequently linked), but also the chemical coupling of structurally related analogs of those organic compounds (e.g., oximes are pre-screened but the analogous aldehydes are linked). Structurally related analogs or organic compounds, however, for the purposes herein, will themselves be organic compounds.

As described above, organic compounds will comprise a chemically reactive functionality (or a site that can be converted to a chemically reactive functionality) to which a linker element may be covalently bound, thereby providing a means for cross-linking two or more organic compounds (or analog thereof) to provide a potential ligand compound. Therefore, linker elements that find use herein will be multifunctional, preferably bifunctional, cross-linking molecules that can function to covalently bond at least two organic compounds together via their reactive functionalities. Linker elements will have at least two, and preferably only two, chemically reactive functionalities that are available for bonding to at least two organic compounds, wherein those functionalities may appear anywhere on the linker, preferably at each end of the linker and wherein those functionalities may be the same or different depending upon whether the organic compounds to be linked have the same or different chemically reactive functionalities. Linker elements that find use herein may be straight-chain, branched, aromatic, and the like, preferably straight chain, and will generally be at least about 2 atoms in length, more generally more than about 4 atoms in length, and often as many as about 12 or more atoms in length. Linker elements will generally comprise carbon atoms, either hydrogen saturated or unsaturated, and therefore, may comprise alkanes, alkenes or alkynes, and/or other heteroatoms including nitrogen, sulfur, oxygen, and the like, which may be unsubstituted or substituted, preferably with alkyl, alkoxyl, hydroxyalkyl or hydroxy groups. Linker elements that find use will be a varying lengths, thereby providing a means for optimizing the binding properties of a ligand compound prepared therefrom.

In particularly preferred embodiments, linker elements may be bis-hydroxylamine compounds, preferably O,O'-diamino-1,4-butanediol, which are useful for chemically coupling aldehyde organic compounds, or any of a variety of different diamine compounds, which are useful for chemically coupling aldehyde organic compounds.

Various chemistries may be employed for chemically coupling organic compounds via a linker element to provide potential ligands for binding to a target biomolecule. For example, many well known chemistries that can be employed for chemically coupling organic compounds via a linker element to form a potential ligand compound include, for example, reductive aminations between aldehydes and ketones and amines (March, *Advanced Organic Chemistry*, John Wiley & Sons, New York, 4th edition, 1992, pp.898–900), alternative methods for preparing amines (March et al., supra, p.1276), reactions between aldehydes and ketones and hydrazine derivatives to give hydrazones and hydrazone derivatives such as semicarbazones (March et al., supra, pp.904–906), amide bond formation (March et al., supra, p.1275), formation of ureas (March et al., supra, p.1299), formation of thiocarbamates (March et al., supra, p.892), formation of carbamates (March et al., supra, p.1280), formation of sulfonamides (March et al., supra, p.1296), formation of thioethers (March et al., supra, p.1297), formation of disulfides (March et al., supra, p.1284), formation of ethers (March et al., supra, p.1285), formation of esters (March et al., supra, p.1281), additions to epoxides (March et al., supra, p.368), additions to aziridines (March et al., supra, p.368), formation of acetals and ketals (March et al., supra, p.1269), formation of carbonates (March et al., supra, p.392), formation of enamines (March et al., supra, p.1284), metathesis of alkenes (March et al., supra, pp.1146–1148 and Grubbs et al., *Acc. Chem. Res.* 28:446–452 (1995)), transition metal-catalyzed couplings of aryl halides and sulfonates with alkenes and acetylenes (e.g., Heck reactions) (March et al., supra, pp.717–178), the reaction of aryl halides and sulfonates with organometallic reagents (March et al., supra, p.662), such as organoboron (Miyaura et al., *Chem. Rev.,* 95:2457 (1995)), organotin, and organozinc reagents, formation of oxazolidines (Ede et al., *Tetrahedron Letts.* 38:7119–7122 (1997)), formation of thiazolidines (Patek et al., *Tetrahedron Letts.* 36:2227–2230 (1995)), amines linked through amidine groups by coupling amines through imidoesters (Davies et al., *Canadian J. Biochem.* 50:416–422 (1972)), and the like.

The step of chemically coupling, via a linker element, at least a portion of the organic compounds identified as described above as being capable of binding to the molecular target or structurally related analogs thereof provides a library of potential ligands for binding to the target molecule that comprise at least two of the organic compounds or analogs thereof and the linker element. The organic compounds incorporated into potential binding ligands may be the same, thereby providing a homomultimer, or different, thereby providing a heteromultimer, and libraries of potential ligands generally comprise both homo- and heteromultimers. Potential ligands for binding to the target molecule are preferably dimeric, however, ligands that find use may also be trimeric, tetrameric, and the like, those compounds being obtained by employing linker elements having more than two chemically reactive functionalities for cross-linking purposes. Ligands and potential ligands for binding to a target biomolecule that find use herein will generally be less than about 4000 daltons in size, usually less than about 3000 daltons in size, more usually less than about 1500 daltons in size, preferably less than about 1000 daltons in size and often less than about 600 daltons in size.

Libraries of potential ligands for binding to the target biomolecule will generally comprise at least 1 potential ligand compound, usually at least about 20 different potential ligand compounds, more usually at least about 100 different potential ligand compounds, preferably at least about 200 different potential ligand compounds, more preferably at least about 500 different potential ligand compounds, most preferably at least 1,000 different potential ligand compounds, often 10,000 or more. Libraries of potential ligand compounds may be constructed such that each individual molecule of the library may be spatially separated from the other molecules of the library (e.g., each member of the library is a separate microtiter well) or two or more members of the library may be physically combined if methods for deconvolution are readily available.

Once obtained, libraries of potential ligands for binding to the target molecule will be screened for the purpose of identifying a member(s) of the library which is capable of binding to the target biomolecule with high affinity. For such purposes, any of the above described screening assays can be employed, wherein preferably an ELISA assay is employed.

For the step of screening a library of potential ligand compounds to identify one or more that bind to a target biomolecule, it will be well within the skill level in the art to determine the concentration of the ligand compounds to be employed in the binding assay. For the most part, the screening assays will employ concentrations of potential ligand compounds ranging from about 0.1 to 500 μM, preferably from about 0.05 to 100 μM, more preferably from 0.05 to 50 μM.

We have herein found that ligand compounds generated by chemically coupling organic compounds that bind to a target biomolecule often exhibit surprising high binding affinities for the target. For the most part, ligand compounds that serve as potential drug lead compounds or may have therapeutic efficacy on their own bind to the target biomolecule with a $K_d$ of about 500 μM or less, usually about 100 μM or less, more usually about 50 μM or less, preferably about 10 μM or less, more preferably about 1 μM or less and most preferably about 0.5 μM or less. However, for various applications, one or more ligand compound(s) having an individual $K_d$ for the target biomolecule of greater than 500 μM may also find use.

Another embodiment of the present invention is directed to a method for inhibiting the interaction between first and second biological molecules which bind to each other, wherein the method comprises contacting a system comprising those molecules with a binding inhibitory amount of a ligand molecule identified by the method described above, wherein the ligand binds to the first biological molecule and inhibits its ability to bind to the second biological molecule. For the most part, the first and second biological molecules will be proteins, nucleic acids, saccharide complexes, and the like, preferably at least one being a protein, more preferably both being proteins. In particularly preferred embodiments, the first or second biological molecule may be CD4 or gp120. In other preferred embodiments, the first biological molecule may be a protein wherein the second biological molecule is a receptor for that protein, a nucleic acid, either DNA or RNA, that binds to that protein or a polysaccharide or the first biological molecule is an enzyme wherein the second biological molecule is a substrate for that enzyme.

Systems that comprise both the first and second biological molecules may be either in vitro or in vivo, wherein the first and second biological molecules are situated such that they are capable of binding to one another. For in vivo applications, the ligand of interest may be administered on its own or in pharmaceutically acceptable media, for example normal saline, PBS, etc. The additives may include bactericidal agents, stabilizers, buffers, or the like. In order to enhance the half-life of the ligand compounds in vivo, the compounds may be encapsulated, introduced into the lumen of liposomes, prepared as colloids, or another conventional technique may be employed that provides for an extended lifetime thereof.

The ligand compounds may be administered as a combination therapy with other pharmacologically active agents or may physically linked to such agents or other carriers. Various methods for administration may be employed. The ligand compounds may be given orally, or may be injected intravascularly, subcutaneously, peritoneally, etc. A "binding inhibitory amount" of ligand compounds will vary widely, depending upon the nature of the first and second biological molecules, the frequency of administration, the manner of administration, the clearance of the compound from the host, and the like. Appropriate binding inhibitory amounts may be determined empirically by those skilled in the art in a routine manner.

Further details of the invention are illustrated in the following non limiting examples.

EXPERIMENTAL

Unless otherwise noted, materials were obtained from commercial suppliers and used without further purifications. Aldehydes were purchased from Aldrich Chemical Company, Inc. (Milwaukee, Wis.). Anhydrous dimethylsulfoxide (DMSO) and acetic acid were purchased from Fischer (Pittsburg, Pa.). Soluble CD4 (sCD4) was purchased from Intracel Corporation (Issaquah, Wash.), gp120 and anti-gp120 antibody were purchased from DuPont (Wilmington, Del.) and o-phenylenediamine peroxidase substrate tablet sets were purchased from Sigma Chemical Co. (St. Louis, Mo.). Reactions were carried out in commercially available Beckman 2 ml deep-well microtiter plates.

Example 1

Pharmacophore Recombination for the Identification of Ligand Compounds Capable of Inhibiting the Interaction between gp120 and CD4

To demonstrate the principle of pharmacophore recombination, we established a biochemical screen for the inhibition of gp120-CD4 binding. This assay measures the ability of small ligand molecules to inhibit the binding of gp120 to sCD4 that is immobilized on a microtiter plate. Binding of sCD4 was quantified with an anti-gp120 antibody conjugated to horseradish peroxidase.

General Procedure for the Synthesis of an Organic Oxime Compound Library

For several reasons, we chose to initially employ O-methyl oximes, rather than aldehydes, for the initial organic compound building block library. First, O-methyl oximes best model the pharmacophore units in the final oxime coupled dimers. Second, O-methyl oximes are more soluble in aqueous solution than their more hydrophobic aldehyde precursors. Also, the oxime functionality is clearly not inherently toxic and does not interfere with good pharmacokinetics or cell permeability since oximes are present in many drugs. Finally, the O-methyl oximes are easily prepared in a single step condensation of aldehydes with O-methyl hydroxylamine, without requiring purification of the resultant product. The chemical condensation of an aldehyde with O-methyl hydroxylamine to provide an organic oxime compound is shown in FIG. 1.

In the first step of the method, the initial oxime building block library was synthesized by separately condensing O-methyl hydroxylamine with 252 different aldehydes in a DMSO solution. The oxime building block library was prepared in a spatially separate fashion in a microtiter plate format such that each well contained a single oxime building block. More specifically, in each well of a microtiter plate, a DMSO solution of an unique aldehyde (0.188 ml, 0.15 M, 0.028 mmol) was added. To this solution, a DMSO solution of O-methyl hydroxylamine (0.083 ml, 0.5 M, 0.042 mmol) was then added followed by addition of a DMSO solution of acetic acid (0.023 ml, 0.5 M, 0.011 mmol). The plates were allowed to sit at room temperature overnight during which time condensation occurred, thereby providing the 252 member library of organic oxime compounds.

Assay to Determine which Organic Oxime Compounds are Capable of Inhibiting the Interaction between gp120 and CD4

The 252 member organic oxime compound population prepared as described above was then screened for the presence of organic compounds capable of inhibiting the interaction between gp120 and CD4 in a standard ELISA assay For the gp120-CD4 ELISA assay, an Immulon-2 microtiter plate was incubated overnight at 4° C. with 70 ng of sCD4 in 100 μl of carbonate buffer. The solution was removed from the plate and washed three times with phosphate buffered saline (PBS) at pH 7.4. The plate was blocked with 150 μl PBS-Tween-BSA (0.5% BSA, 0.05% Tween-20) for 1 h at room temperature and then washed again. gp120 (1 ng) in 50 μl of PBS and 50 μl of test organic oxime compound (3 mM), 40 μl PBS, 10 μl were added and incubated for 1 h at room temperature. The plate was then washed and 100 μl of anti-gp120 conjugated horseradish peroxidase was added and incubated for 1 h at room temperature. The bound gp120 was then quantitated with o-phenylenediamine as a substrate.

Figure 2:
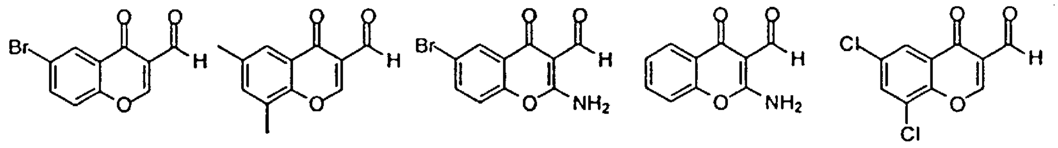
FIG. 2 shows a variety of organic aldehyde pharmacophore molecules identified as being capable of inhibiting the interaction between CD4 and gp120.
Figure 2:
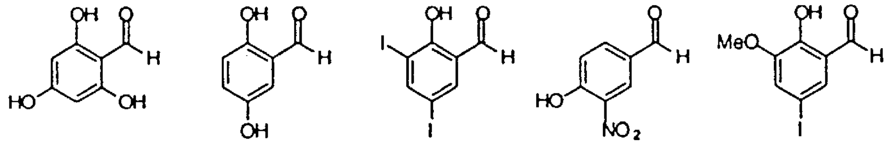
Figure 2:
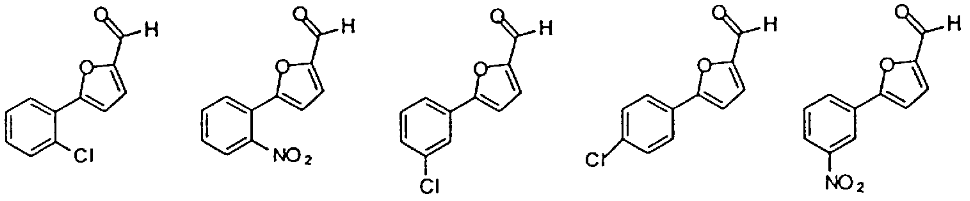
Figure 2:
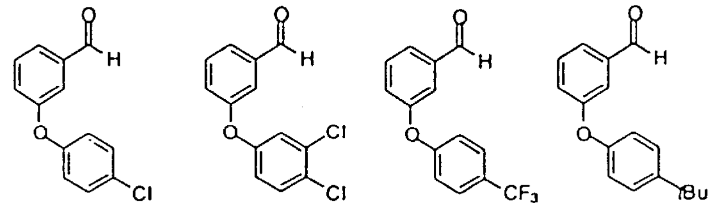
Figure 2:
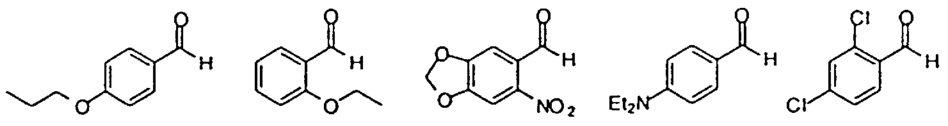
Figure 2:
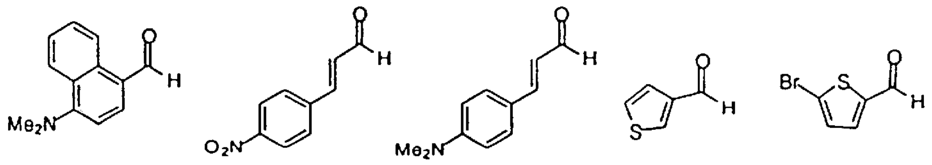

The results of these assays demonstrated that 30 of the 252 organic oxime compounds were capable of inhibiting the interaction between gp120 and CD4, wherein the approximate $EC_{50}$ values ranged from about 20 μM to 500 μM. The structurally related aldehyde analogs of 30 of these oximes showed diverse structural motifs including chromones, phenols and furans (see FIG. 2).

Linkage of the Top 30 Structurally Related Aldehyde Analogs to Produce a Library of Potential Ligands and Screening of those Potential Ligands for the Ability to Inhibit the Interaction between gp120 and CD4

Figure 3:
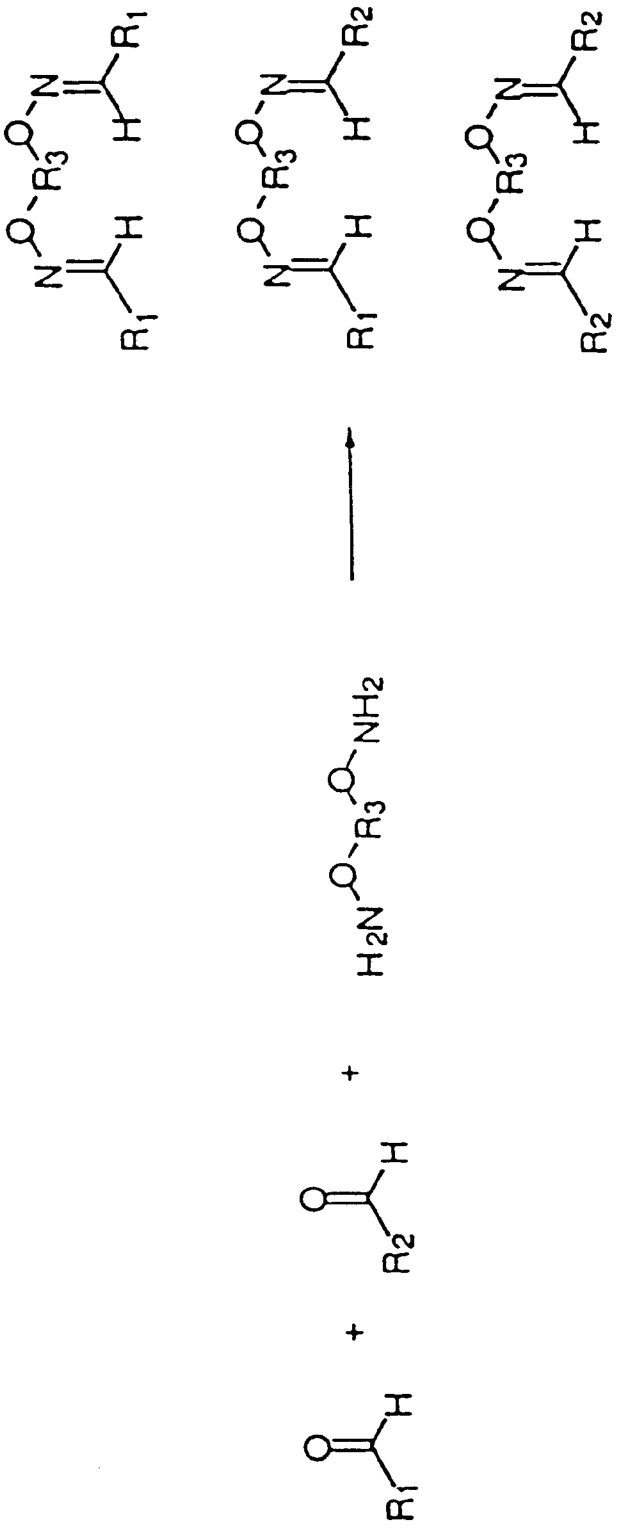
FIG. 3 shows chemistry useful for chemically coupling two aldehydes via a bis-hydroxylamine linker element to produce both heterodimeric and homodimeric oxime compounds.

Each of the 30 structurally related aldehydes analogs corresponding to the 30 organic oxime compounds identified above as being capable of inhibiting the interaction between gp120 and CD4 were individually coupled to each of the other 29 aldehydes with a variety of linkers to produce a library of potentially ligands for binding to the target molecule. Each of the 30 individual aldehydes was linked with another aldehyde through a bis-hydroxylamine linker to obtain the library of linked potential ligands. Each aldehyde combination was kept spatially separate, but an equimolar mixture of five different bis-hydroxylamine linkers were used in each coupling reaction to provide a 450-member library of linked potential ligands. The chemistry used for preparation of the ligands is shown in FIG. 3 showing the synthesis of both homodimers and heterodimers.

The five linkers employed each consisted of two hydroxylamine groups tethered to an aliphatic chain having either two, three, four, five or six methylene units. This allowed us to evaluate any distance dependency the two pharmacophores may have in the binding site. Linkers were prepared as follows. To a round-bottomed flask was added alkyl dibromide (20.2 mmol), N-hydroxyphthalimide (36.8 mmol, ~1.8 equiv) and dimethylformamide (90 ml). The flask was cooled to 0° C. and 1,8-diazabicyclo[5.4.0]undec-7-ene (40.5 mmol) was added dropwise with stirring. The reaction was allowed to warm to room temperature and was then stirred overnight. The reaction mixture was then poured into 1M HCl (500 ml). The resulting white solid precipitate was washed with water (3×50 ml) and methanol (3×50 ml) and sent onto the next step without further purification.

13.9 mmol of the crude bis-N-alkoxyphthalimide was then added to a round-bottomed flask in combination with dimethoxyethylene glycol (150 ml). To another flask was added hydrazine monohydrate (41.8 mmol, 3 equiv.) and dimethoxyethylene glycol (100 ml). The suspension of bis-N-alkoxyphthalimide was added slowly with stirring to the hydrazine solution. The flask was refluxed for 3 h, allowed to cool to room temperature and the resulting precipitate was filtered away. The remaining supernatant solution was concentrated and the resulting yellowish-oil was purified by Kugelrohr distillation (0.01 mm Hg, 60–70° C.) and column chromatography (89:9:2 $CHCl_3$/MeOH/$NH_4OH$).

For O,O'-diamino-1,4-butanediol), the general synthesis procedure described above was followed. IR (film from $CH_2Cl_2$): 3412.8, 3310.0, 2942.7, 2866.3 $cm^1$. $^1H$ NMR (400 MHz, $CDCl_3$): δ5.31 (br s, 4H), 3.65 (m, 4H), 1.57 (m, 4H). $^{13}C$ NMR (400 MHz, $CDCl_3$): δ75.5, 24.8. Anal. Calcd for $C_4H_{12}O_2N_2$: C, 39.99; H, 10.07; N, 23.32. Found: C, 40.17; H, 9.90; N, 23.12.

Once the five linkers were obtained, the 450 linked aldehyde combinations were prepared as follows. In each well, a DMSO solution of each of two different aldehydes (0.045 ml, 0.15 M, 0.007 mmol each) was added. To this solution, a DMSO solution of an equimolar mixture of the five linkers (0.025 ml, 0.3 M of each linker, 0.007 mmol) was added followed by a DMSO solution of acetic acid (0.005 ml, 0.5 M, 0.003 mmol). The plates were allowed to sit at room temperature overnight to allow for potential ligand formation.

Figure 4:
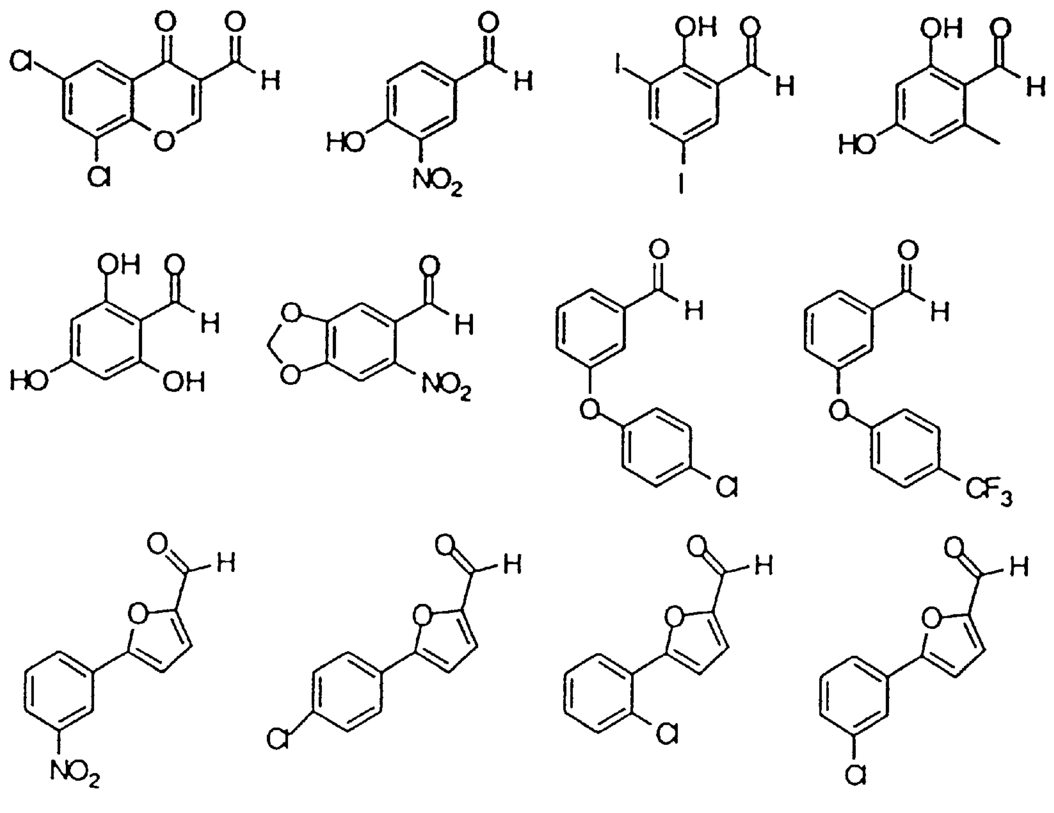
FIG. 4 shows a variety of aldehyde pharmacophores found to be highly efficient in dimeric form for inhibiting the interaction between CD4 and gp120.

Each of the 450 members of the potential ligand library was then tested at a concentration of 100 μM each (i.e., a concentration that is 10-fold more dilute than the concentration employed in the initial oxime monomer screen) for the ability to inhibit the interaction between gp120 and CD4 using the ELISA assay described above. The results from these assays demonstrated that more than 300 of the 450 members of the potential ligand library showed greater than 50% inhibition activity at the concentration employed. When the 450 members of the potential ligand library were tested at a concentration of 1 μM each for the ability to inhibit the interaction between gp120 and CD4, 17 of the ligands showed greater than 50% inhibitory activity at that concentration. The chemical structures of 12 of the 17 most active aldehyde precursors are shown in FIG. 4.

Evaluation of Linker Length Dependence on Activity

Figure 5:
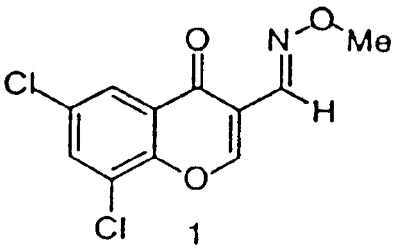
FIG. 5 shows an organic O-methyl oxime compound found to be particularly effective in dimeric form for inhibiting the interaction between CD4 and gp120.

The 17 linked aldehyde combinations with the greatest activity were then resynthesized as described above with a unique linker per well (85 separate wells) so as to evaluate any linker-length dependency on binding. Screening each of the 85 ligand compounds at 1 μM each showed that ligands that incorporated pharmacophore 1 (see FIG. 5) were more potent than the other ligands and that there indeed was a dependence upon linker length. Specifically, ligands with linkers having either 4 or 5 methylene units were much more active than ligands with linkers having 6 methylene units, whereas ligands with linkers having either 2 or 3 methylene units were only slightly more active than ligands with linkers having either 4 or 5 methylene units.

Biological and Analytical Characterization of Representative Ligands

Figure 6:
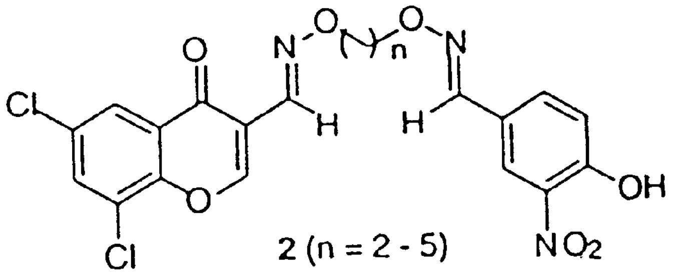
FIG. 6 shows a specific ligand having particularly high activity for inhibiting the interaction between CD4 and gp120.

One of the ligands that exhibited strong activity for inhibiting the interaction between gp120 and CD4 (as shown in FIG. 6) was resynthesized with each of the five different linkers on a large scale and was then purified by column chromatography. Column chromatography purification enabled isolation of the heterodimer from the homodimer.

Large scale synthesis of organic oxime compounds was performed as follows. To a flame-dried round-bottomed flask was added aldehyde (0.82 mmol) and DMSO (8 ml). A 0.9 M O-methyl hydroxylamine (1.4 ml) was then added and the reaction mixture was allowed to stir at room temperature overnight. The reaction was poured into methylene chloride (50 ml), washed with $H_2O$ (3×20 ml), dried and concentrated. Silica gel chromatography provided the pure organic oxime compounds.

The oxime compounds made by this method were characterized as follows.

(1) O-methyl oxime of 6-nitropiperonal

Reaction of 6-nitropiperonal with O-methyl hydroxylamine provided predominantly one oxime isomer which was purified by silica gel chromatography (10:90, EtOAc/hexanes). $^1H$ NMR (400 MHz, $CDCl_3$): δ8.61 (s, 1H), 7.53 (s, 1H), 7.37 (s, 1H), 6.15 (s, 2H), 4.00 (s, 3H). Anal. Calcd for $C_9H_8O_5N_2$: C, 48.22; H, 3.60; N, 12.50. Found: C, 48:40; H, 3.75; N, 12.56.

(2) O-methyl oxime of 6,8-dichloro-3-formylchromone

Reaction of 6,8-dichloro-3-formylchromone provided 1:1 cis/trans isomers which were isolated by silica gel chromatography (20:80, $CH_2Cl_2$/hexanes).

Isomer 1: $^1H$ NMR (400 MHz, $CDCl_3$): δ8.48 (s, 1H), 8.24 (s, 1H), 8.12 (d, 1H, J=2.5), 7.75 (d, 1H, J=2.5), 3.97 (s, 3H). Anal. Calcd for $C_{11}H_7O_3NCl_2$: C, 48.56; H, 2.59; N, 5.15. Found: C, 48.44; H, 2.47; N, 5.03.

Isomer 2: $^1H$ NMR (400 MHz, $CDCl_3$): δ9.45 (s, 1H), 8.12 (d, 1H, J=2.5), 7.75 (d, 2H, J=2.5), 4.07 (3H). Anal. Calcd for $C_{11}H_7O_3NCl_2$: C, 48.56; H, 2.59; N, 5.15. Found: C, 48.45; H, 2.49; N, 5.11.

Large scale synthesis of oxime ligands was performed as follows. To a flame-dried round-bottom flask was added 10 ml of DMSO and 1.03 mmol of each of the two aldehydes to be incorporated into the ligand. After all solids were dissolved, a solution of the appropriate linker (1.24 mmol) in 1 ml of DMSO was added dropwise, followed by the addition of acetic acid (0.72 mmol). The reaction mixture was allowed to stir at room temperature overnight. The reaction was then poured into methylene chloride (50 ml), washed with $H_2O$ (3×20 ml), dried and concentrated. Silica gel chromatography provided the isolated homo/heterodimers. Cis/trans isomers, when present, were not separated and were purified as mixtures of isomers. The oxime dimers made by this method were characterized below.

(1) Oxime heterodimer of 6,8-dichloro-3-formylchromone and 6-nitropiperonal, linker containing 4 methylene units The heterodimer was separated from the homodimers by silica gel chromatography (20:80, EtOAc/hexanes). The heterodimer was isolated and characterized as a 1:1 mixture of cis/trans isomers. Anal. Calcd for $C_{22}H_{17}O_8N_3Cl_2$: C, 50.59; H, 3.28; N, 8.05; Found: C, 50.70; H, 3.40; N, 7.89.

Isomer 1: $^1H$ NMR (400 MHz, $CDCl_3$): δ9.42 (s, 1H), 8.55 (s, 1H), 8.00 (s, 1H), 7.67 (m, 2H), 7.39 (s, 1H), 7.27 (s, 1H), 6.09 (s, 2H), 4.22 (m, 4H), 1.84 (m, 4H).

Isomer 2: $^1H$ NMR (400 MHz, $CDCl_3$): δ8.54 (s, 1H), 8.41 (s, 1H), 8.16 (s, 1H), 7.99 (s, 1H), 7.67 (s, 1H), 7.40 (s, 1H), 7.24 (s, 1H), 6.08 (s, 2H), 4.22 (m, 4H), 1.83 (m, 4H).

(2) Oxime heterodimer of 6,8-dichloro-3-formylchromone and 6-nitropiperonal, linker containing 5 methylene units The heterodimer was separated from the homodimers by silica gel chromatography (20:80, EtOAc/hexanes). The heterodimer was isolated and characterized as a 1.5:1 mixture of cis/trans isomers. Anal. Calcd for $C_{23}H_{19}O_8N_3Cl_2$: C, 51.51; H, 3.57; N, 7.83; Found: C, 51.68; H, 3.70; N, 7.66.

Isomer 1: $^1H$ NMR (400 MHz, $CDCl_3$): δ8.62 (s, 1H), 8.47 (s, 1H), 8.24 (s, 1H), 8.10 (s, 1H), 7.74 (s, 1H), 7.73 (s, 1H), 7.37 (s, 1H), 6.14 (s, 2H), 4.20 (m, 4H), 1.8 (m, 4H), 1.53 (m, 2H).

Isomer 2: 1H NMR (400 MHz, $CDCl_3$): δ9.47 (s, 1H), 8.61 (s, 1H), 8.11 (s, 1H), 7.75 (s, 2H), 7.48 (s, 1H), 7.33 (s, 1H), 6.14 (s, 2H), 4.30 (t, 2H, J=6.6), 4.20 (m, 2H), 1.80 (m, 4H), 1.53 (m, 2H).

These purified heterodimers and homodimers were then tested as described above for the ability to inhibit the interaction between gp120 and CD4. The results of these assays demonstrated that heterodimers shown in FIG. 6 having a linker containing anywhere from 2 to 5 methylene units exhibited $EC_{50}$'s in the range from 0.6 to 1.5 μM and showed 10- to 20-fold enhancement in inhibitory activity over the organic compound shown in FIG. 5 (EC50 in the range of about 10–15 μM). The other organic compound that was incorporated into the heterodimer had an EC50 of greater than 50 μM.

The heterodimers shown in FIG. 6 having linkers containing from 2 to 5 methylene units are of comparable potency to the most potent compounds that have been identified to date that block the CD4/gp120 interaction (Tanaka et al., *J. Antibiotics* 50:58 (1997), Sun et al., *J. Antibiotics* 49:689 (1997), Jarvest et al., *Bio. Med. Chem. Lett.* 3:2851 (1993) and Chen et al., *Proc. Natl. Acad. Sci. USA* 89:5872 (1992)). In addition, these ligand heterodimers are considerably less complex than previously identified compounds with comparable activity. Further optimization of the optimal building block and linker combinations could presumably be accomplished by evaluating a larger range of linkers with enhanced rigidity or by incorporating analogs of the optimal aldehyde precursors.

Example 2

Figure 7:
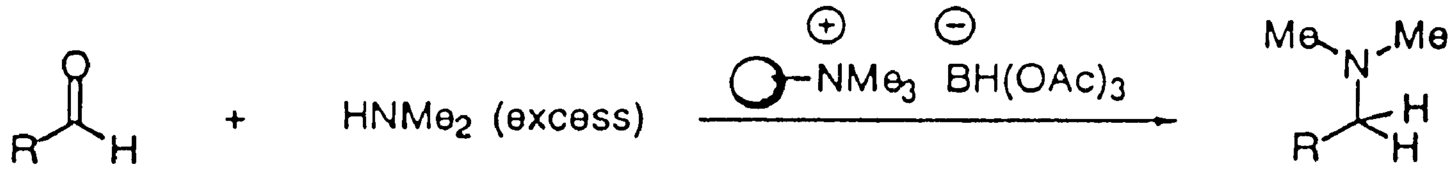
FIG. 7 shows a synthetic reaction wherein an aldehyde is reacted with a dimethylamine in the presence of support-bound triacetoxyborohydride to give rise to an N,N-dimethylamine organic compound.

Pharmacophore Recombination Using N,N-Dimethylamine Organic Compounds and Diamine Linkers In addition to the use of aldehydes and oximes for the pharmacophore recombination method as described above, additional chemistries also find use. In this example, the organic compound building blocks are N,N dimethylamine compounds that are prepared by reductive amination of starting aldehydes and dimethylamine using support-bound triacetoxyborohydride (Kaldor et al., *Tetrahedron Lett.* 37:7193–7196 (1996)). The chemistry of these reactions is shown in FIG. 7. Removal of the support-bound reducing agent by filtration followed by concentration to remove the volatile, excess dimethylamine then provides the pure N,N-dimethylamine monomer building blocks. Alternatively, the N,N-dimethylamine building blocks may be obtained by reduction using a sodium borohydride-based reducing agent in solution. The resulting amine product is then isolated from the excess reducing agent or aldehyde by passing down an acidic ion exchange column. The amine product is then obtained by elution from the ion exchange column with a volatile amine such as ammonia followed by concentration.

Figure 8:
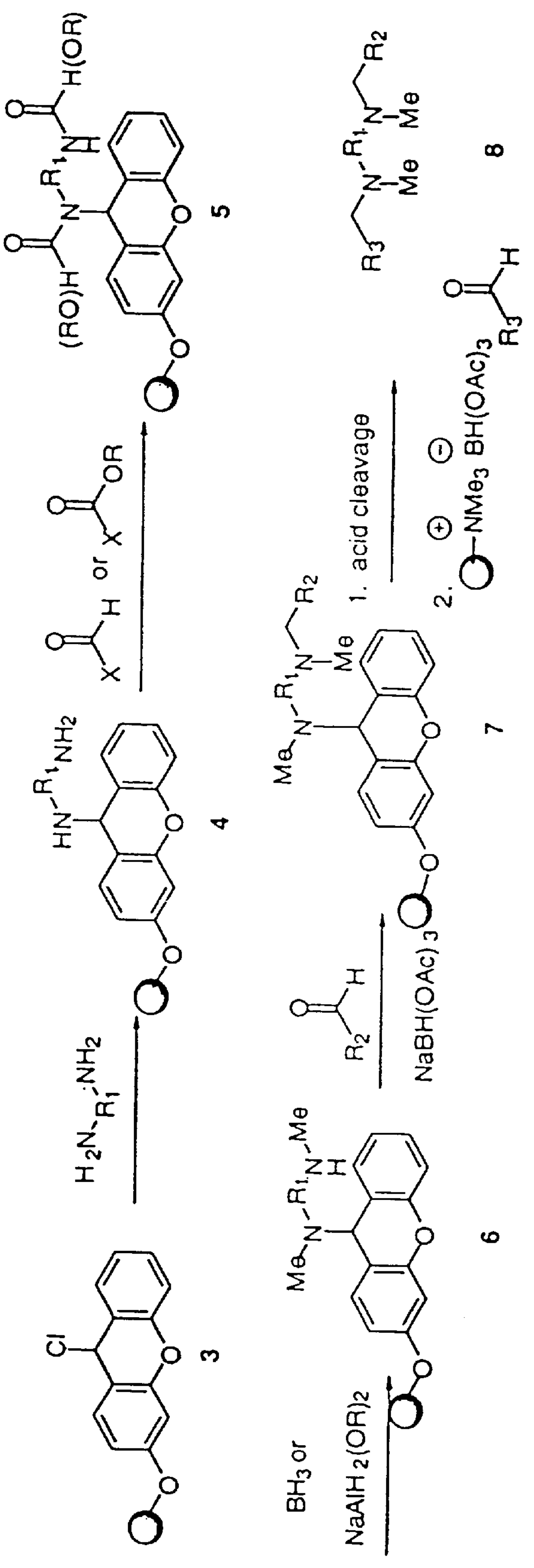
FIG. 8 shows a chemical synthesis sequence resulting in the production of a ligand of the present invention.

Linkage of the N,N-dimethylamine organic compound building blocks can be accomplished through the use of diamine linkers of which hundreds are commercially available and many more can be readily prepared using well known methodology. The commercial availability of the diamine linkers allows rapid optimization of linker length, rigidity and orientation. An exemplary synthesis sequence is shown in FIG. 8. Specifically, support-bound chloride (3) (or other support-bound halide) is treated with excess of a diamine to provide an amine-derivatized support (4). Acylation of the amine functionality then provides support-bound formamide or carbamate (5). Reduction then provides support-bound secondary amine (6). Reductive amination then introduces one of the pharmacophore elements (7). Acid treatment then releases a secondary amine from the support, which can then be treated with the second pharmacophore monomer and sodium triacetoxyborohydride to provide the desired pharmacophore heterodimer (either support-bound reagent or alternative scavenging methods may be employed). Initial attachment of the diamine to the support can be accomplished using other support-bound alkyl halides or could be accomplished by reductive amination of a support-bound aldehyde or ketone. Fewer linkers are available that contain two secondary amine groups, but these can also be incorporated in this case, the acylation step (4 to 5 in FIG. 8) and the subsequent reduction step (5 to 6 in FIG. 8) would be eliminated.

The foregoing description details specific methods which can be employed to practice the present invention. Having detailed such specific methods, those skilled in the art will well enough know how to devise alternative reliable methods at arriving at the same information in using the fruits of the present invention. Thus, however, detailed the foregoing may appear in text, it should not be construed as limiting the overall scope thereof; rather, the ambit of the present invention is to be determined only by the lawful construction of the appended claims. All documents cited herein are expressly incorporated by reference.

What is claimed is:

1. A method for identifying candidate lead drug ligands that inhibit the binding of members of a complementary pair of biological molecules, said method comprising:

contacting both members of said pair of biological molecules with individual members of a library of potential ligands either sequentially or simultaneously, each potential ligand comprising at least two organic compounds that are inhibitors of binding and are linked to a linker element, and selecting ligands that inhibit the binding of said pair of biological molecules to a greater extent than either of the individual organic compounds linked to said linker element, wherein said library of potential ligands is produced by:

(a) screening a population of organic compounds that are capable of being chemically coupled by a linker element to identify a subpopulation of said organic compounds which inhibit binding of said pair of biological molecules; and (b) chemically coupling compounds selected from the group consisting of said subpopulation of organic compounds and structurally related analogs thereof with at least one linker element, to provide a library comprising at least 20 different potential ligands, where said population of organic compounds comprise O-substituted oximes (>C═N—O—) or aldehydes.

2. The method according to claim 1, wherein said linker element comprises a bis-hydroxylamine.

3. The method according to claim 1, wherein said pair of biological molecules are proteins.

4. The method according to claim 1, wherein one of said pair of biological molecules is a protein and the other of said pair of biological molecules is selected from the group consisting of a nucleic acid and a polysaccharide.

5. The method accordinig to claim 1, wherein one of said pair of biological molecules is a protein, a nucleic acid or a saccharide.

6. The method according to claim 5, wherein one of said pair of biological molecules is a protein.

7. The method according to claim 6, wherein said protein is an enzyme, a hormone, a cytokine, a chemokine or a receptor.

8. The method according to claim 1, wherein one of said pair of biological molecules is an enzyme and the other of said pair of biological molecules is a substrate for said enzyme.

9. The method according to claim 1, wherein at least one of said organic compounds of said subpopulation of organic compounds inhibits binding to one of said pair of biological molecules with a $K_d$ of 10 mM or lower.

10. The method according to claim 1, wherein at least one of said organic compounds of said subpopulation of organic compounds inhibits binding to one of said pair of biological molecules with a $K_d$ of 1 mM or lower.

11. The method according to claim 1, wherein said potential ligand binds to one of said pair of biological molecules wilt a $K_d$ of 500 $\mu$M or lower.

12. The method according to claim 1, wherein said potential ligand binds to one of said pair of biological molecules with a $K_d$ of 50 $\mu$M or lower.

13. The method according to claim 1, wherein said population of organic compounds comprises organic compounds with molecular weight of less than about 1000 Daltons.

14. The method according to claim 13, wherein said population of organic compounds comprises organic compounds with molecular weight of less than about 500 Daltons.

15. The method of claim 1, wherein step (a) is accomplished by an in vitro biological assay.

16. The method of claim 15, wherein the in vitro biological assay is a competitive assay comprising: contacting one member of said pair of biological molecules with an assay molecule that binds to said biological molecule, in the presence of one of said organic compounds and measuring the inhibition of the binding of the assay molecule to said biological molecule.

17. The method of claim 16, wherein the assay molecule is an antibody to said biological molecule.

18. The method of claim 17, wherein the assay is an ELISA assay.

19. The method of claim 18, wherein step (a) is accomplished by ELISA assay and said ELISA assay is conducted at from 0.1 to 500 $\mu$M of each organic compound.

20. The method of claim 1, wherein selecting ligands that inhibit the binding of said pair of biological molecules to a greater extent than either of the individual organic compounds linked to said linker element is accomplished by an in vitro biological assay.

21. The method of claim 20, wherein the assay is an ELISA assay.

22. The method of claim 1, wherein said library of potential ligands for binding to one of said pair of biological molecules comprises at least about 100 different members.

23. The method of claim 1, wherein each of the members of said population of organic compounds comprises a common chemical functionality to which said linker element may bond.

* * * * *